United States Patent
Rizvi et al.

(10) Patent No.: US 9,978,250 B2
(45) Date of Patent: May 22, 2018

(54) DETECTION OF HYGIENE COMPLIANCE

(71) Applicant: Sidra Medical and Research Center, Doha (QA)

(72) Inventors: Avez Ali Rizvi, Doha (QA); Saif Reza Ahmed, Doha (QA); Deepak Kaura, Doha (QA)

(73) Assignee: SIDRA MEDICAL AND RESEARCH CENTER, Doha (QA)

( * ) Notice: Subject to any disclaimer, the term of this patent is extended or adjusted under 35 U.S.C. 154(b) by 24 days.

(21) Appl. No.: 15/131,932

(22) Filed: Apr. 18, 2016

(65) Prior Publication Data
US 2017/0004699 A1 Jan. 5, 2017

Related U.S. Application Data

(60) Provisional application No. 62/148,510, filed on Apr. 16, 2015.

(51) Int. Cl.
*G08B 21/24* (2006.01)
*G01J 5/00* (2006.01)
*G06F 19/00* (2018.01)

(52) U.S. Cl.
CPC .......... *G08B 21/245* (2013.01); *G01J 5/0025* (2013.01); *G06F 19/327* (2013.01); *G01J 2005/0077* (2013.01)

(58) Field of Classification Search
CPC ................. G08B 21/245; G01J 5/0025; G01J 2005/0077; G06F 19/327
See application file for complete search history.

(56) References Cited

U.S. PATENT DOCUMENTS

| | | | | |
|---|---|---|---|---|
| 6,038,331 | A * | 3/2000 | Johnson | G06K 9/00375 134/113 |
| 7,936,275 | B2 * | 5/2011 | Bolling | G06F 19/327 338/34 |
| 9,418,536 | B1 * | 8/2016 | Felch | G08B 21/245 |
| 2002/0019709 | A1 * | 2/2002 | Segal | G07C 1/10 702/45 |
| 2009/0024023 | A1 * | 1/2009 | Welches | A61B 18/201 600/424 |
| 2011/0169646 | A1 * | 7/2011 | Raichman | G08B 21/245 340/573.1 |
| 2014/0327545 | A1 * | 11/2014 | Bolling | G08B 21/245 340/573.1 |
| 2014/0375457 | A1 * | 12/2014 | Diaz | G08B 21/245 340/573.1 |

OTHER PUBLICATIONS

Alexander Schlaefer, Et al; Evaluating Hand Disinfection with Alcohol-Based Hand Sanitizers Using Thermal Imaging, 2016, 2nd Workshop on Fail Safety in Medical Cyber-Physical Systems, pp. 174-181; http://ceur-ws.org/Vol-1559/paper23.pdf.*

* cited by examiner

*Primary Examiner* — Brian Zimmerman
*Assistant Examiner* — Sara Samson
(74) *Attorney, Agent, or Firm* — Tarter Krinsky & Drogin LLP (57) ABSTRACT

The present technology relates to apparatuses, methods and systems for detecting hygiene compliance, particularly in hospital and clinical settings, where hospital acquired infections (HAIs) are of concern. A temperature signature can be determined and then used to ascertain whether a user is compliant with a given hygiene standard. The present technology also relates to sanitizing compositions used in conjunction with such apparatuses, methods and systems.

18 Claims, 4 Drawing Sheets

DETECTION OF HYGIENE COMPLIANCE

BACKGROUND

The present technology relates to apparatuses, methods and systems in connection with the detection of hygiene compliance, including hand hygiene compliance, particularly in restaurants, food services and other food handling, schools, laboratories and research facilities, hospital and clinical settings.

Hospital Acquired Infections (HAIs) account for billions of dollars of direct healthcare cost to hospitals annually. In the United States, the costs range from a conservative $5.7 billion to as high as $31.5 billion. HAIs can lead to longer hospital stays, more repeated hospital stays and increased risk of complications and mortality for patients. Similarly, there are associated costs related to preserving hygiene and preventing transmission of illness with regard to restaurants and food services institutions, laboratories and research facilities.

It has been shown that implementation of simple and effective hand washing and other hygiene techniques can significantly reduce the burden of HAIs and other infections.

Unfortunately, consistent and reliable healthcare worker adoption of hygiene use is a difficult goal to achieve. Due to the fast pace of a typical healthcare worker's workday, hygiene methods are not always implemented consistently or adhered to strictly. Confirmation of hygiene compliance via tracking alone does little to confirm proper use of hygiene techniques. All of the current hand hygiene utilities promise both hardware and software approaches to track hygiene usage and report data without real solutions in reducing non-compliance or addressing proper hand hygiene techniques. In fact, a study in 2010 found that the overall median compliance rate with hand hygiene guidelines in hospital care is only 40%.

Thus, a need exists for improved apparatuses, methods and systems for detection of compliance, including but not limited to hand hygiene compliance, that can be effectively and consistently implemented and that can result in significant improvements in compliance, with measurable and results, including decreased rates of infection and costs, and increased patient well-being.

SUMMARY OF THE DISCLOSED TECHNOLOGY

In certain embodiments, the present technology is directed to a method of measuring hygiene, comprising: (a) contacting a portion of a user's body with a sanitizing composition that creates a temperature signature on the surface of the portion of the user's body having contact with the sanitizing composition; (b) determining the temperature signature; and (c) comparing the temperature signature with a known temperature signature for the user or the sanitizing composition.

In certain embodiments, the present technology is directed to a sanitizing composition comprising alcohol. In certain embodiments, the present technology is directed to a sanitizing composition comprising: (a) alcohol; (b) water; and (c) an additional ingredient chosen from a vitamin, a humectant, an emollient, a binding agent or an emulsifier.

In certain embodiments, the present technology is directed to an apparatus for measuring hygiene, comprising: (a) a device that measures a temperature signature; (b) a processing unit that compares the obtained temperature signature with a known temperature signature indicating an acceptable level of hygiene; and (c) an output indicator that indicates whether the temperature signature equals or exceeds the acceptable level of hygiene.

In certain embodiments, the present technology is directed to a method of measuring hygiene, comprising: (a) imaging a portion of a user's body to obtain a temperature signature; (b) comparing the obtained temperature signature with a known temperature signature indicative of an acceptable level of hygiene; and (c) providing feedback to the user communicating the result of (b).

In certain embodiments, the present technology is directed to a system for measuring hygiene, the system comprising: (a) an apparatus that determines a first temperature signature for a user and a second temperature signature for the same user; (b) a processing unit that compares the first temperature signature and the second temperature signature and determines whether the two temperature signatures are acceptably close to each other; and (c) an output visual or sound display that communicates the result of (b).

DETAILED DESCRIPTION

The present technology relates to the reduction of HAIs in restaurants, food services and other food handling settings, schools, laboratories and research facilities, hospital and clinical settings. As used herein, the term "HAI" refers to not only hospital acquired infections, but any infections acquired in any of the settings mentioned herein. In certain embodiments, this is addressed through the use of technologies such as infrared camera technology. The growth of camera technology—specifically with smaller yet robust infrared cameras—has allowed for novel apparatuses, methods and systems to solve hygiene compliance related issues in multiple settings.

As used herein, the term "skin" includes all of the outer surfaces of the body, including not only the skin covering any surface of the body, but also the scalp, keratinous layers such as nails and hair, and the mucosa. In certain embodiments, the compositions, methods and apparatuses herein are directed to the skin of a user's hands or arms, as these areas are particularly important for hygiene in hospital and clinical settings. However, the technology herein is not limited to any particular part of a user's body.

As used herein, the term "user" refers to any individual who has the need to adopt robust hygiene practices, including but not limited to a worker in a research facility, laboratory or healthcare worker. As used herein, the term "healthcare worker" refers to a physician, nurse, or any other individual who works in a research, hospital or clinical setting and who has need to adopt robust hygiene practices, whether or not that person comes into actual physical contact with patients.

The term "thermal imaging or infrared imaging" as used herein is a type of imaging used to determine radiation or temperature data in the infrared and near-infrared range of the electromagnetic spectrum. The radiation or temperature data can be retrieved via single images, sequences of images, or by a video stream of recorded images; as well as via other information that is not in the form of an image. This data can be combined with other software techniques to provide information on compliance of hand hygiene use with a particular sanitizing composition as discussed herein.

The term "hand hygiene station" used herein refers to any area in which an ABSS or NCSS dispenser is present and hand hygiene can conceivably be observed. This area can be present, for example (but not limited to), within a hospital setting, hallway, outpatient clinic setting, patient room, patient waiting area, or elevator corridor.

As used herein, the concept of "hand gestures" or "gestures" relates to the action of using the user's hands in a particular action or shape to trigger an event or sequence of events as recognized via a computer or mobile device's camera video/video-streaming technology.

The term "client device" or sometime "electronic device" or "device" as used herein is any type of instrument capable of computing data. Non-limiting examples of client devices include; personal computers (PCs), workstations, laptops, tablet PCs including the iPad, mobile phones or mobile devices, or generally any electronic device capable of computing data. Certain types of client devices that are portable and easily carried by a person from one location to another can sometimes be referred to as a "mobile device". Some non-limiting examples of mobile devices include; mobile thermal imaging cameras, mobile infrared cameras, such as FLIR One™ cellular or mobile phones, smart phones, tablet computers, laptop computers, wearable computers including watches, glasses, or other accessories incorporating any level of computing.

As used herein, the term "database" means a digital collection of data or information stored on a data store such as a hard drive. The present technology is directed, in certain embodiments, to apparatuses, methods and systems to store, link, and modify information such as user profile information. For the purposes of the present disclosure, a database can be stored on a remote server and accessed by a mobile device through a data network (e.g., wifi or cloud) or alternatively in some embodiments the database can be stored on the mobile device or remote computer itself (i.e., local storage). A "data store" as used herein can contain or comprise a database (i.e., information and data from a database can be recorded into a medium on a data store).

In certain embodiments herein, the technology is directed to methods and systems for ensuring that a user complies with a hygiene standard set by an organization such as a school, restaurant, research facility, hospital or clinical care facility.

Temperature Signature

In various embodiments, the methods and apparatuses herein are directed to measurement of hygiene comprising a temperature signature. As used herein, "temperature signature" means a set of data that provides information and that is measured, calculated or demonstrates any of the following:

(1) the temperature measured on a certain point or points on the surface of the user's body (for example, the hands) at a given time that is a "baseline" time—that is, before the user has specifically washed or sanitized the surface, either with the sanitizing solution or water or some other cleaner in relation to the present technology;

(2) an average temperature calculated based on measurements made on two or more points on the surface of the user's body as described in (1) above;

(3) the temperature measured on a certain point or points on the surface of the user's body (for example, the hands) at a given time that is a "sanitized" or "clean" time—that is, after the user has specifically washed or sanitized the surface, either with the sanitizing solution or water or some other cleaner in relation to the present technology;

(4) an average temperature calculated based on measurements made on two or more points on the surface of the user's body as described in (3) above;

(5) the difference between the "baseline" temperature or temperatures of (1) or (2) and the "sanitized" or "clean" temperature or temperatures of (3) or (4);

(6) The rate of change (that is, the measure of degrees of change over a certain period of time) from the "baseline" temperature or temperatures as described above to the "sanitized" temperature or temperatures as described above, or to any additional temperatures at any additional given times;

(7) A visual indicator or depiction of any of (1) to (6) above, such as, for example, a video image or thermal image scan (such as an image showing temperature contrasts or different temperatures represented by different colors or different qualities of images, or an infrared image) or a binary image such as an "on" or "off" indicator or a light that when illuminated indicates a temperature above or below a certain threshold, or at a certain threshold, or within a certain range; or (8) An aural (heard) depiction of any of (1) to (6) above, such as, for example, a chime, beep, buzz, vibration or other discernible aural or sound indicator that when deployed indicates a temperature above or below a certain threshold, or at a certain threshold, or within a certain range.

Figure 1:
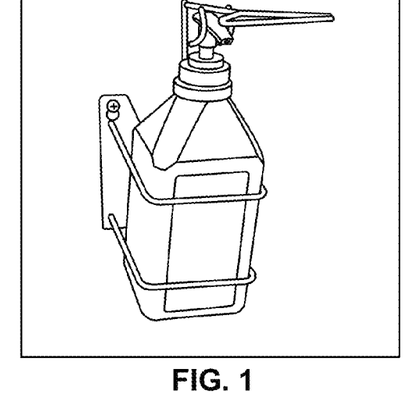
FIG. 1 shows an exemplary sanitizing composition in accordance with the present technology.
Figure 2:
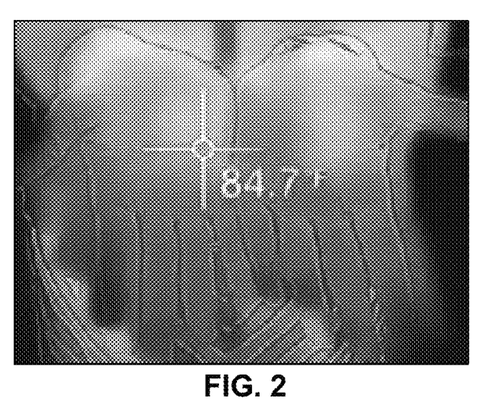
FIG. 2 shows a thermal image of a user's hands taken at a "baseline" ("dirty") stage before application of a sanitizing composition herein.
Figure 3:
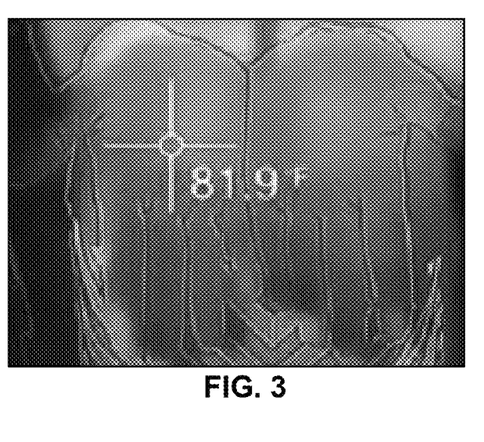
FIG. 3 shows a thermal image of a user's hands taken at a "clean" stage after application of a sanitizing composition herein.
Figure 4A:
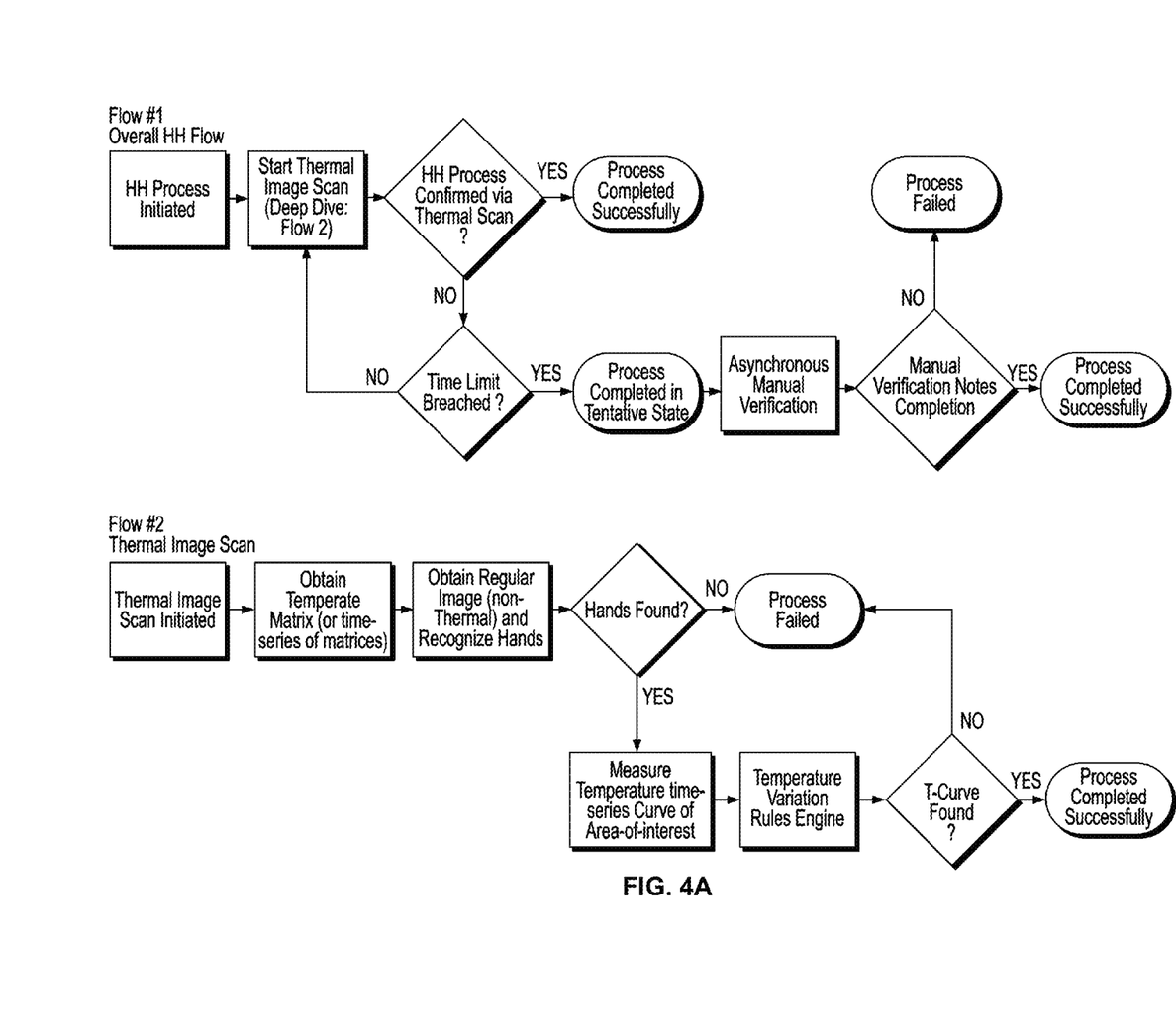
FIG. 4a-4c show exemplary workflows of systems in accordance with the present technology.
Figure 4B:
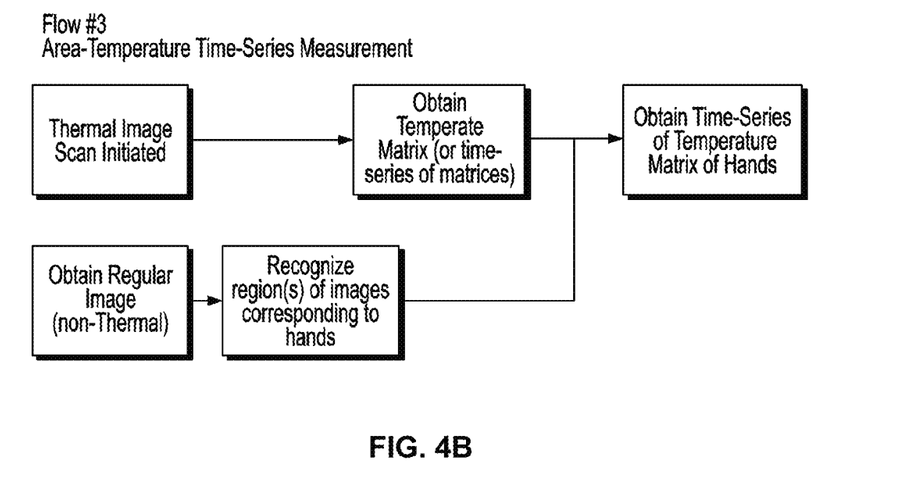
Figure 4C:
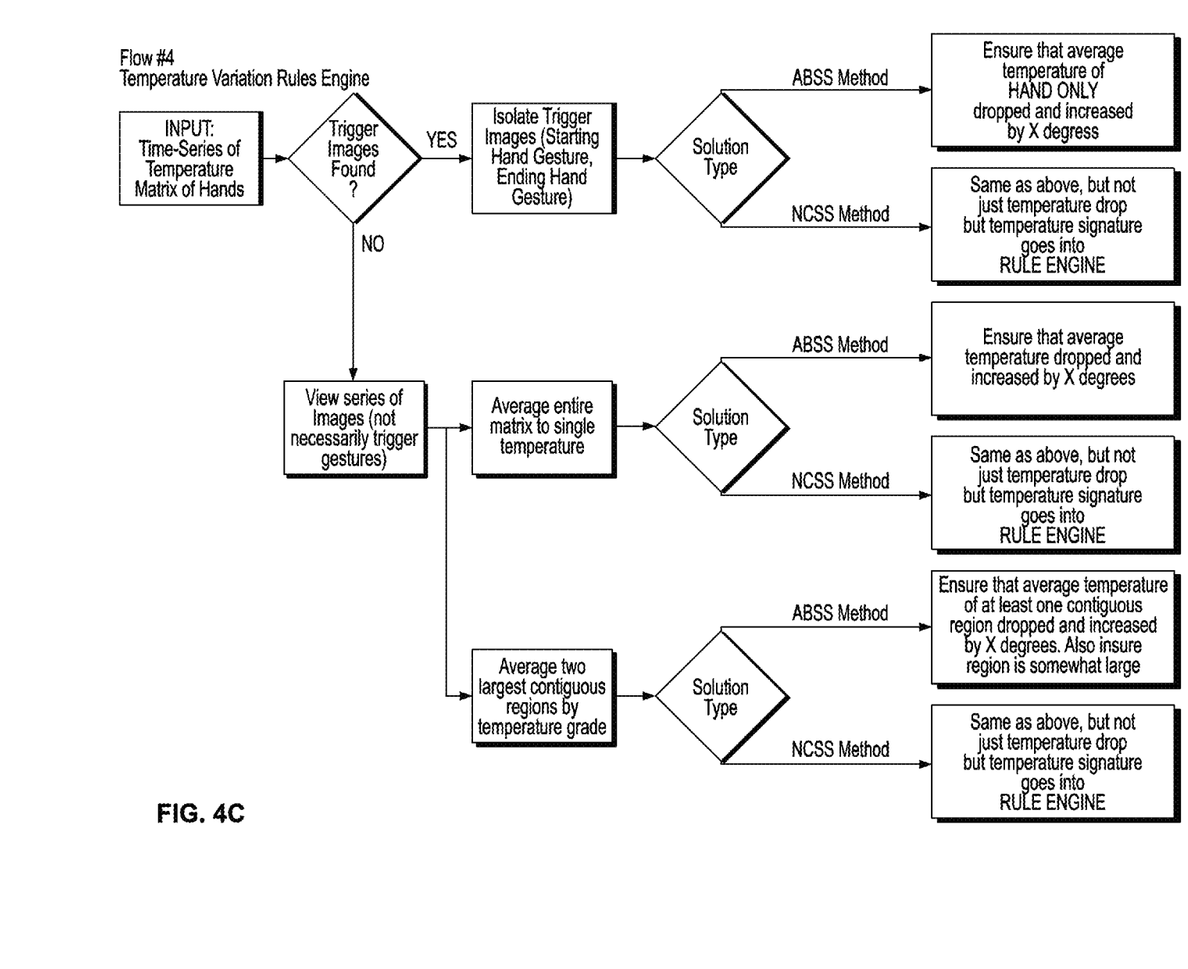

In certain embodiments, as for example in those shown in FIG. 4 herein, the temperature signature can be calculated based on any information obtained from the user. As an example a temperate matrix (or series of matrices over time) can provide at least part of the desired information. The temperature matrix is an n×m matrix of temperatures, where n and m are the width and height, respectively, of the sensor's field of view. The temperature matrix is particularly useful because the temperature is not expected to be uniform across the surface of the skin, and thus, working with the temperature of a single point on the skin would not be sufficient. Instead, with a matrix of temperature data as obtained from, for example, a thermal camera, better predictability can be achieved. The data can be associated with specific points on the skin, in certain embodiments in conjunction with a photograph upon which image recognition has been performed, thus permitting the user to associate temperatures to known parts of the skin, for example, specific known parts of a hand.

In another example, a thermal or non-thermal image of the portion of the user's body of interest may provide at least part of the desired information.

In certain embodiments, the sound indicator or visual indicator (or both, as the case can be) can be audible or visible, respectively, to the user such that the user immediately knows whether he or she has satisfied the required threshold value for compliance with the hygiene standard. In certain embodiments, the sound indicator or visual indicator (or both, in certain embodiments) can be audible or visible, respectively, to a location separate from where the user is located; for example, in a central location where the user can be monitored remotely as he changes locations throughout the work shift and engages the compliance methods, systems or apparatuses herein.

A temperature signature can be, in various embodiments, unique to a user, unique to a particular sanitizing composition, unique to both a user and a particular sanitizing composition, or unique to a user, a particular sanitizing composition and any additional identification factors. Thus, each user can have a unique temperature signature associated with each sanitizing solution. In certain embodiments a sanitizing composition can be associated with one temperature signature in connection with one user, but can be associated with a different temperature signature in connection with a different user; or can create a temperature signature in association with any of these factors plus any additional factors, including but not limited to: time of day, location of the user or any apparatus in accordance with the present technology; different body parts of the user (e.g., hand versus arm, or left hand versus right hand); specific hygiene requirements for a given task (for example, different temperature signatures can be required for certain tasks (e.g., handling of raw meat or raw vegetables, or serving food in a restaurant or food service application); or for handling certain items (e.g., contacting live animals, certain chemicals, or bacteria or viruses in a research setting); or for contacting certain individuals such as customers or patients, e.g., children, the elderly, patients in intensive care or the emergency room, patients with suppressed immunity); or any other condition of the sanitizing composition, apparatuses, systems or methods herein, user or location of any of the foregoing.

Sanitizing Composition

In various embodiments, the technology herein contemplates a sanitizing composition that can be applied to the skin of a user. In certain embodiments, the present technology is directed to methods of measuring hygiene comprising applying or a sanitizing composition, or methods of measuring the effect that a sanitizing composition has on the skin of the user.

Advantages of the sanitizing compositions described herein include ease of application, ease of storage and dispensing to a user, and low cost. In certain embodiments, a sanitizing composition according to the present technology comprises the following:

(a) a solvent (which in certain embodiments yields a reaction, including but not limited to a hypothermic reaction or hyperthermic reaction); and (b) an alcohol;

In various embodiments, the solvent may comprise water (for example, deionized water), a polar or nonpolar solvent, or an anionic, nonionic or ionic solvent. In various embodiments, the solvent comprises about 40 to about 95%, about 50 to about 95%, or about 60 to about 80% alcohol. Exemplary additional ingredients include isopropyl alcohol, ethyl alcohol, specially denatured alcohol (SDA) and other cosmetic grade, organic or nonorganic, monohydric or polyhydric alcohols; benzalkonium chloride, humectants including glycerin or propylene glycol, octyl isononanoate, methylcellulose, hydroxypropyl methylcellulose (for example, Benecel™ available from Ashland), emollients including isopropyl myristate, and natural ingredients including vitamins (e.g., vitamin E), aloe vera, tocopherol, tocopheryl acetate, emulsifiers including carbomer or aminomethyl propanol, gelling agents, colorants or fragrances.

In various embodiments, the sanitizing composition is in a form that is economical to produce and transport, can be stored at room temperature (or in various embodiments, higher or lower than room temperature, e.g., in temperatures typical of long term storage or refrigeration) without deteriorating or breaking down, and can easily be applied to the skin of a user. In certain embodiments, the sanitizing composition can comprise a solid, liquid or gas, including any of the following: gel, mousse, foam, lotion, cream, suspension, emulsion, ampule, capsule, caplet, encapsulate, sachet, balm, semi-solid, roll-on stick, vapor, spray (aerosol or non-aerosol), atomized substance or propellant medium.

In certain embodiments, the sanitizing composition is applied to the user's skin and then rinsed off, dried off or wiped off, e.g., with a cloth or paper towel. In other embodiments, the sanitizing composition is applied and then nothing further is done; for example, the sanitizing composition is allowed to penetrate into the skin or to dry or evaporate on its own. In certain embodiments, an advantage of a sanitizing composition herein is its ability to evaporate quickly (in various embodiments, within about 10 or about 5 seconds), subsequently cooling the skin. In certain embodiments, once applied on skin, the sanitizing composition evaporates and cools the skin surface in the process. This level of cooling is determined by using specifically tuned cameras such as, for example, infrared cameras or thermal imaging, to monitor the rate of cooling over a set period of time. In certain embodiments, the temperature signature comprises the step of "tagging" the temperature on the surface of the user's body prior to application of the sanitizing composition, and again afterwards.

In certain embodiments, the sanitizing composition is an alcohol-based sanitizing solution ("ABSS"). As used herein, the term "alcohol-based" means containing at least about 40% alcohol. Examples of alcohols that are useful include, but are not limited to: isopropyl alcohol, ethyl alcohol, butyl alcohol, pentanol (amyl alcohol), cetyl alcohol, ethylene glycol, propylene glycol, glycerol, erythritol, threitol, xylitol, mannitol, sorbitol, volemitol, allyl alcohol, geraniol, propargyl alcohol, inositol, menthol and any other alcohol. As used herein, the term "sanitizing solution" means a solution that a user applies to the outer surface of his or her body, including but not limited to the hands, and that is expected to clean the surface by reducing the number of microbes on the surface. In certain embodiments, a sanitizing solution herein comprises any of the following: alcohol, water or an antimicrobial (for example, antibacterial, antiviral or antifungal) composition.

In other embodiments, the sanitizing composition need not be alcohol-based, and indeed need not comprise any alcohol at all. In certain embodiments, a sanitizing composition herein has any or all of the following general properties: it significantly increases or decreases the temperature of skin surface when used in hand hygiene with respect to baseline (or before the use of the chemical composition), allowing the temperature change to be captured by thermal imaging. The term "significantly" as used herein refers to the scientific definition and means any temperature change outside of physiologic variation detectable by thermal imaging techniques.

A sanitizing composition herein can, in certain embodiments, cool the skin, heat the skin, or both cool and heat the skin. In other embodiments, it need not change the temperature of the skin, but may indicate otherwise that the hygiene event has occurred. For example, in certain embodiments, the sanitizing composition can contain any composition that indicates a change—including, but not limited to, pH, a tingling sensation, or a change in image under a thermal imaging or infrared technique.

In certain embodiments, the thermal imaging or infrared techniques discussed herein can be used to log and store the associated temperature changes, creating a unique temperature signature for a user or a sanitizing composition. The reaction can, in certain embodiments, including one or more cooling or heating steps, or multiple cooling or heating steps; each a certain time apart and of different magnitudes, or any combination thereof. In certain embodiments, such heating or cooling patterns resulting from the above individual endothermic or exothermic reactions would be the "signature" of a particular sanitizing composition, and would be readable by machines, even if not detectable by humans. More complex signatures would prevent false reads brought by ancillary causes of temperature changes (room temperature, touching a cold item such as a can of soda, etc.). FIG. 4 shows an exemplary workflow of such a method or system.

In other embodiments, the sanitizing composition may include, for example, a pH indicator (for example, gentian violet, malachite green, thymol blue, methyl yellow, bromophenol blue, methyl orange, methyl red, methyl purple, azolitmin, bromocresol purple, bromothymol blue, phenol red, naphtholphthalein, phenolphthalein or the like); or a composition that provides a cooling or tingling sensation when used (for example, menthol or menthol derivatives such as menthol with a carboxamide derivative, cyclohexanecarboxamide dimethyl menthyl succinimide, menthyl lactate, menthone glycerin acetal, menthoxypropanediol; neoisomenthol, neomenthol, isomenthol; or on-menthol derivatives such as phenol derivatives, e.g., thymol, eugenol or capsaicin.

Apparatus

In various embodiments, the present technology is directed to an apparatus for measuring hygiene.

In certain embodiments, the apparatus comprises: (a) a device that measures a temperature signature; (b) a processing unit that compares the obtained temperature signature with a known temperature signature indicating an acceptable level of hygiene; and (c) an output indicator that indicates whether the temperature signature equals or exceeds the acceptable level of hygiene.

In other embodiments, the apparatus merely measures the temperature signature and displays information via an output indicator, without a comparison with a known temperature signature.

The device can be any device that measures the temperature signature, as discussed previously. In various embodiments, the device can comprise any of the following: a thermometer, an infrared detector, a heat detector, a thermal image scanner, a non-thermal scanner or a camera. In certain embodiments, the device comprises a thermal camera that provides both a thermal image and a non-thermal ("traditional") image, wherein one or both of the thermal image and the non-thermal image are available either as a combined image or as a time series such as a moving video). In such an embodiment, the non-thermal image can be useful in assistance with the user's image recognition, which often relies on color regions and skin detection via color regions.

In certain embodiments, the processing unit includes a computer. As used herein, the term "computer" refers to a machine, apparatus, or device that is capable of accepting and performing logic operations from software code. The terms "software," "software code" and "computer software" refer to any set of instructions written using some human-readable computer language and operable to cause a computer to perform an operation. Software code can be operated on by a "rules engine" or processor, which executes one or more rules on data to produce an outcome. Thus, the methods and systems herein can be performed by a computer based on instructions received by computer software.

In various embodiments, the computer includes any of the following: a processing unit, a memory (which can include logic or software for carrying out any of the functions described herein), a communication interface, as well as other conventional computer components including, but not limited to: an input device (such as a keyboard, touchscreen or microphone), an output device (such as a screen, display or speaker). The computer can also include logic (e.g., http web server logic) or is programmed to format data, accessed from local or remote databases or other sources of data and content.

In certain embodiments, an apparatus as described according to the embodiments herein comprises a device that is configured to detect a trigger event. As used herein, the term "trigger event" means any event (for example, a hand gesture, other physical gesture, engagement of a switch or voice-activated command) that indicates when a hygiene event has begun or ended. For example, in certain embodiments a user can wave his hand (or any body part whose temperature signature is to be calculated by the apparatus) in a manner that constitutes a trigger event, such that the apparatus begins gathering the images or other information that it uses to calculate the temperature signature of the user. In another embodiment, an apparatus herein is operated at least in part by voice-activated command; in such a situation, a user can interact with the system verbally, and thus can advantageously initiate the trigger event while his or her body part is are soiled, for example, hands soiled with blood.

The output indicator can comprise, in various embodiments, a visual indicator or aural or sound indicator as discussed previously. In certain embodiments, compliance can be indicated with the illumination of a light or a certain sound, while non-compliance can be indicated with the illumination of a different light, or a different sound, or the lack of a light or sound. For example, in certain embodiments, if the system determines that the user has complied with the hygiene standard, a green light could illuminate, whereas if the system determines that the user has not complied with the hygiene standard, a red light could illuminate.

In certain embodiments, the apparatus can be either fixed in a particular location (e.g., the user can periodically approach and use the apparatus) or can be portable or wearable, that is, is small enough that a user can carry it on his or her person while going about daily activities; in such cases the apparatus can be removably attached to the user, or can be carried by the user.

In certain embodiments, the apparatus is integrated into an overall system that comprises multiple apparatuses for tracking multiple users. For example, an exemplary process and system allows for the detection of users as they interact with certain settings, which include patient encounter areas with Bluetooth, WiFi, infrared, near field sensors, and the like. For example, the detection process can use Bluetooth 4.0 Low Energy (BTLE) "beacons" that will be attached near patient settings with the actual location to be determined based on each particular setting. In one example, the wearable computing software will use the "electronic leash" application profile capabilities of the BTLE Proximity Profile (PXP) and Find Me Profile (FMP) to determine the location of each beacon in relation to the location of the wearable computer device. A pre-determined location database associated with each beacon will then associate the user with the specific location and effectively track the user.

In certain embodiments, an apparatus herein is operated by a processor running on a computer which can be a server or a mobile device such as a wearable computer device (e.g., smart glasses, augmented reality device or any wearable electronic device that includes a camera). In certain embodiments, a wearable computer device can provide a platform to track a user's hygiene participation, periodically remind the user of proper hygiene techniques, and provide each user with an individual account with information including a profile and past compliance.

Methods and Systems

In a simple embodiment, a method herein comprises measuring the temperature of a point on a user's body part (such as his or her hand) in a "baseline," "pre-wash" ("dirty") time, then applying a sanitizing composition herein to the user's body part, and then measuring a temperature of the point in a "post-wash" ("clean" or "sanitized") time, and calculating the difference between the "pre-wash" and "post-wash" temperatures. A difference in a certain number of degrees or fraction of degrees can, in certain embodiments, indicate that an acceptable level of hygiene has been achieved.

In certain embodiments, a method herein will measure more than just a temperature difference on a point on the user's body, and can take other factors into account. For example, another method herein comprises the following steps: the user subjects the portion of his or her body to be scanned to the apparatus. This can be achieved by, in various embodiments, initiating a trigger event (for example, waving the hands in a certain configuration designed to trigger the apparatus to begin gathering data; or by the user's moving into an area within physical proximity of the apparatus or, in the case of a wearable apparatus on the user's body, of a device that detects the proximity of the apparatus), or by other action of the user, including for example, turning on the power or pressing a button on the apparatus indicating readiness to begin the hygiene compliance analysis; the apparatus then obtains the information it requires to calculate the temperature signature (in various embodiments, a thermal image scan, a photo, a temperature measurement). The computer control unit analyzes the data gathered, calculates the temperature signature and determines whether it complies with the hygiene standard—for example, whether it satisfies the temperature variation rules.

In various embodiments, the method can be executed in any of the following manners:

(1) The system takes a "pre-washing" or "baseline" scan at a given point in time (for example, when the user is first hired by the healthcare facility). Periodically during a typical workday, every time that the user washes his or her hands or other body part, the apparatus takes a "during-washing," (or in certain embodiments, "post-washing") "clean" or "sanitized" scan and determines whether hygiene compliance has been achieved and communicates the result, with the result determining whether the system is finished with the determination (that is, the user is in compliance) or whether the wash has to be repeated; or (2) The system itself determines the level of hygiene compliance required for all users (based on standard values rather than individual user baseline data) and indicates at a pre-determined time (for example, at a given time on the clock, or within a certain time interval before a known and programmed event such as a scheduled surgery or a particular patient's appointment) when the user must submit to having a scan taken. At that point, the system scans the user's hands or other body part, determines whether hygiene compliance has been achieved, and communicates the result, with the result determining whether the system is finished with the determination (that is, the user is in compliance) or whether the user must.

In other embodiments, a system herein is non-automated—that is, it can be a system in which a camera is simply used to scan a user's body part (including but not limited to the hands) and the results are presented in a visual or sound output. In such embodiments, the system can be in a wearable or otherwise portable form, that an administrator or operator may carry around and use to perform spot checks; alternatively, such a system can be fixed in place (for example, affixed to a sanitizer solution dispenser or on a wall or door) and users can be required to approach it to submit to periodic spot checks. In certain embodiments, the system may be configured such that anyone passing within a certain zone (for example, students, patients or workers walking down a hallway or entering a lunchroom or laboratory or operating room) can be subjected to a passive reading to ensure compliance with a hygiene standard.

In certain embodiments, the system relies on a "during-washing" scan—that is, compliance is determined by taking a scan while the user is washing, and measuring the level of temperature drop over the skin surface area of interest. In certain embodiments, this measurement must be taken either while the washing is occurring, or immediately (within a few seconds, e.g., within about 5, about 10 or about 15 seconds) after the washing has stopped, in order to capture the temperature drop, which may be fleeting.

In certain examples (e.g., in Example (2) above), the system is capable of taking "real-time" measurements of user compliance. That is, in various embodiments, a system herein comprises numerous units located throughout a healthcare facility, optionally in addition to wearable apparatuses attached to each user, such that at any time determined by the system, a user's hygiene compliance can be determined.

In certain embodiments, a system in accordance with the embodiments herein can utilize various web data interface techniques such as Common Gateway Interface (CGI) protocol and associated applications (or "scripts"), Java® "servlets," i.e., Java® applications running on the system to present information and receive input from user devices. In certain embodiments, a system herein comprises one or more computers, devices, databases, associated backend devices, and the like, communicating (wired and/or wireless) and cooperating to perform some or all of the functions described herein. In certain embodiments, the system further includes or communicates with account servers (e.g., email servers), mobile servers or media servers.

In certain embodiments, the systems described herein are implemented in relation to tracking and ensuring compliance of hygiene using the sanitizing compositions discussed herein with infrared camera technology. These data include, but are not limited to, any of the following: subcategorized employment information including full name, department of employment, position of employment, particular shifts of employment, and other data inclusive to build specific employee profiles. Other data can include infrared camera temperatures, rate of temperature change, time of sampling, gesture recognition, video of hand hygiene compliance, and time-stamping data in relation to tracking users in the hospital setting. The systems as described herein are unique as they allow streamlined tracking and verification on compliance of hand hygiene participation using the sanitizing compositions and novel thermal imaging temperature signature capabilities of infrared cameras.

Another advantage of the systems herein is reducing ambiguity and tracking the user for compliance. Ambiguity can result when determining compliance of a particular task. Hygiene ambiguity results when systems cannot definitively determine compliance. The systems herein can determine not only whether a person was near a hygiene station or even if said station was used; but also eliminate ambiguity about whether a sanitizing composition was used for the purpose of hand hygiene. In the embodiments herein that include recording the hygiene process through thermal imaging, this ambiguity is removed and compliance is assured.

In certain embodiments, a system herein comprises any of the following:

1. A stand alone station that uses software algorithms with infrared or thermal imaging to detect compliance once the sanitizing composition is applied appropriately; or 2. A mobile solution that uses software algorithms with infrared or thermal imaging that is independent of the hygiene station, and detects hygiene compliance to determine whether a sanitizing composition has been applied appropriately.

Either method will use the above mentioned thermal imaging techniques coupled with particular software to determine compliance of hygiene.

Another advantage of the systems herein is determining appropriateness of hygiene. Known systems on occasion claim some indirect metric to judge compliance; however, the removal of an actual observable solution further distances those techniques from judging appropriateness. The approach herein of tracking hygiene use, coupled with thermal imaging data, permits the methods and systems herein to delineate whether hygiene protocol was followed appropriately. For example, in certain embodiments by following a heat map of particular hand regions and determining the evaporation temperature signature distribution, it is possible to assess whether appropriate amounts of the sanitizing composition was used to satisfy appropriate germicidal targets and ultimately infectability.

In certain embodiments, a software mapping scheme can be created with further research to quantify and validate appropriateness using the methods and systems discussed herein. Thus, the present technology can assess appropriateness of use in a superior manner when compared to other methods.

Central Repository

In certain embodiments, the overall system can maintain a database for each entity with categorized parties and locations. For example, a patient transporter could be a specific Party Type. A nurse would be another Party Type. Specific locations could also be stored. This database would be available to align hand hygiene compliance to specific clients and locations. For example, if a patient transporter encountered a patient in the Emergency Room, the system would automatically query the associated profile of the patient transporter in the appropriate patient transporter category database and detect the location based on the appropriate location database. The central repository would contain a mapping joining artifacts with party types and party-types with specific parties. In certain embodiments, the central repository can also contain all previously defined thermal imaging artifacts and associated information.

EXAMPLE 1

A sanitizing composition in accordance with the present technology was prepared and used by 10 individuals. Each individual applied the composition to his or her hands. Each measured the temperature on the surface of his or her hands in the "baseline" (also referred to herein as "dirty") state (before application of any solution) and then immediately after the application (within about 5 seconds). Results are shown in the Table below.

TABLE 1

| Subject | Before ("Dirty") Temperature | Immediately After ("Clean") Temperature | Temperature Difference |
|---|---|---|---|
| 1 | 86.5 | 84 | 2.5 |
| 2 | 74 | 71.5 | 2.5 |
| 3 | 96.3 | 92.3 | 4 |
| 4 | 85.3 | 83.3 | 2 |
| 5 | 89.5 | 87 | 2.5 |
| 6 | 84.1 | 82 | 2.1 |
| 7 | 87.4 | 84.7 | 2.7 |
| 8 | 80 | 78.8 | 5.1 |
| 9 | 89.1 | 84 | 5.1 |
| 10 | 89.4 | 87.1 | 2.3 |

As can be seen from the Table, when users apply the solutions of the present technology to the skin, a temperature difference is seen from the "pre-treatment" or "before" ("dirty") time to the "after" ("clean") time. In certain embodiments, the temperature signature for a given user will include data indicating temperature information immediately after application of the solution—generally within about 3 seconds, within about 5 seconds, or within about 10 seconds.

EXAMPLE 2

In an exemplary method herein, a thermal image scan is made of a portion of a user's body (for example, the hands). In this example, the user puts his or her hands into the apparatus and allows them to be scanned. The temperature signature is obtained (for example, a temperate matrix or time-series of temperate matrices can be measured)

These exemplary methods are further depicted in the flowchart attached FIG. 4.

Although the present technology has been described in relation to particular embodiments thereof, these embodiments and examples are merely exemplary and not intended to be limiting. It will be apparent to one of ordinary skill in the art that aspects of the technology, as described above, may be implemented in many different forms of compositions, systems, software, firmware, and hardware in the implementations illustrated in the Figures. The present technology should, therefore, not be limited by the specific disclosure herein, and can be embodied in other forms not explicitly described here, without departing from the spirit thereof.

What is claimed:

1. A method for determining whether a user has complied with hygiene requirements, comprising:

(a) creating an initial temperature signature representing the temperature of the surface of a portion of a user's body;

(b) contacting the user's body with a sanitizing solution that alters the temperature of said portion of the user's body;

(c) creating a second temperature signature of said portion of the user's body after contact with the sanitizing solution; and (d) determining whether the portion of the user's body has been sufficiently sanitized by comparing the differences between the initial temperature signature and the second temperature signature to a predetermined set of requirements.

2. The method of claim 1, wherein the portion of the user's body is the hand.

3. The method of claim 1, wherein the sanitizing solution comprises alcohol and water.

4. The method of claim 1, wherein the step of creating an initial temperature signature comprises the measurement of temperature at a plurality of points on said portion of the user's body.

5. The method of claim 1, wherein the step of determining whether the portion of a user's body has been sufficiently sanitized by comparing the differences between the initial temperature signature and the second temperature signature comprises comparison of the temperature at a plurality of points in the initial temperature signature to the temperature at substantially the same plurality of points in the second temperature signature.

6. The method of claim 1, wherein the initial temperature signature and the second temperature signature are created using thermal imaging.

7. The method of claim 1, wherein the step of determining whether the portion of a user's body has been sufficiently sanitized by comparing the differences between the initial temperature signature with the second temperature signature comprises comparison of the average temperature of a plurality of points in the initial temperature signature to the average temperature of a plurality of points in the second temperature signature.

8. The method of claim 1, wherein the second temperature signature includes a time component that corresponds to temperature change measured over a period of time.

9. The method of claim 1, wherein the initial temperature signature is created prior to application of the sanitizing solution and the second temperature signature is created within about 3 to about 10 seconds after application of the sanitizing solution.

10. An apparatus for measuring hygiene requirement compliance, comprising:
(a) a thermal imaging device that creates a temperature signature associated with a portion of a user's body;
(b) a database for creating a plurality of user profiles, and for receiving and associating user data with the user profiles, including user data comprising the temperature signature;
(c) a processing unit that obtains a second temperature signature from a thermal imaging device and compares the obtained temperature signature to a temperature signature stored in the database for the user, and determines whether the differences between the two signatures are sufficient such that an acceptable level of hygiene has been achieved; and
(d) an output indicator that indicates to the user whether an acceptable level of hygiene has been achieved.

11. The apparatus of claim 10, wherein the thermal imaging device comprises one or more of an infrared detector, a thermal image scanner, a camera capable of recording IR images, and a camera capable of recording IR video.

12. The apparatus of claim 10, wherein the temperature signature comprises a matrix of surface temperatures measured on one or more regions of the imaged portion of the user's body.

13. The apparatus of claim 10, wherein the wherein the temperature signature comprises the average surface temperature of two or more points measured on the imaged portion of the user's body.

14. The apparatus of claim 10, wherein the imaged portion of the user's body comprises the hand.

15. The apparatus of claim 10, wherein the second temperature signature is provided by a second thermal imaging device.

16. The apparatus of claim 10, wherein the output indicator provides the user with an image of the portion of the user's body showing the differences between the two temperature signatures.

17. The apparatus of claim 10, wherein the database includes (i) a plurality of temperature signatures unique to a user, (ii) data to determine the appropriate signature to be used for a specific user when using a specific sanitizing solution; and (iii) criteria to be applied in comparing each signature to a second temperature signature.

18. The apparatus of claim 10, wherein the database includes temperature signatures for different parts of the user's body.

* * * * *